(12) United States Patent
Trombly et al.

(10) Patent No.: US 10,434,252 B2
(45) Date of Patent: *Oct. 8, 2019

(54) WIRELESS STRAIN GAUGE/FLOW SENSOR

(71) Applicant: STMicroelectronics, Inc., Coppell, TX (US)

(72) Inventors: Nicholas Trombly, Chicago, IL (US); Patrick Furlan, Hawthorn Woods, IL (US)

(73) Assignee: STMicroelectronics, Inc., Coppell, TX (US)

( * ) Notice: Subject to any disclaimer, the term of this patent is extended or adjusted under 35 U.S.C. 154(b) by 655 days.

This patent is subject to a terminal disclaimer.

(21) Appl. No.: 14/983,113

(22) Filed: Dec. 29, 2015

(65) Prior Publication Data

US 2016/0129183 A1 May 12, 2016

Related U.S. Application Data

(62) Division of application No. 13/553,541, filed on Jul. 19, 2012, now Pat. No. 9,539,389.

(Continued)

(51) Int. Cl.
*A61M 5/172* (2006.01)
*A61M 5/168* (2006.01)
(Continued)

(52) U.S. Cl.
CPC ........ *A61M 5/172* (2013.01); *A61M 5/16877* (2013.01); *A61M 5/1456* (2013.01); *A61M 5/14244* (2013.01); *A61M 5/16854* (2013.01); *A61M 5/3134* (2013.01); *A61M 2205/0244* (2013.01); *A61M 2205/0294* (2013.01); *A61M 2205/332* (2013.01); *A61M 2205/3317* (2013.01); *A61M 2205/3334* (2013.01); *A61M 2205/3355* (2013.01); *A61M 2205/3368* (2013.01); *A61M 2205/3372* (2013.01); *A61M 2205/3569* (2013.01); *A61M 2205/3592* (2013.01); *A61M 2205/50* (2013.01); *A61M 2205/6009* (2013.01); *A61M 2205/8243* (2013.01)

(58) Field of Classification Search
CPC .... A61M 5/00; A61M 5/168; A61M 5/16895; A61M 5/16877; A61M 2205/244; A61M 2205/3334; A61M 2205/35; A61M 2205/3507; A61M 2205/3523; A61M 2205/3576; A61M 2205/3592; A61M 2205/6063; A61M 2205/6072; A61M 2205/6081
See application file for complete search history.

(56) References Cited

U.S. PATENT DOCUMENTS 6,796,955 B2  9/2004 O'Mahony et al.
7,337,678 B2  3/2008 Thakre et al.
(Continued)

*Primary Examiner* — Andrew M Gilbert
(74) *Attorney, Agent, or Firm* — Seed IP Law Group LLP

(57) ABSTRACT

A flow rate sensor is provided in a wireless, leadless package. The flow rate sensor includes a MEMs sensor coupled to an ASIC and an antenna. The flow rate sensor is powered by radiation received from a control module adjacent the flow rate sensor. The flow rate sensor is placed within a fluid and monitors the flow rate of the fluid. The control module is not in the fluid and receives flow rate data from the flow rate sensor.

19 Claims, 12 Drawing Sheets

Related U.S. Application Data

(60) Provisional application No. 61/596,631, filed on Feb. 8, 2012.

(51) Int. Cl.
    *A61M 5/145*     (2006.01)
    *A61M 5/31*     (2006.01)
    *A61M 5/142*     (2006.01)

(56) References Cited

U.S. PATENT DOCUMENTS

| | | |
|---|---|---|
| 7,462,161 B2 | 12/2008 | O'Mahony et al. |
| 7,811,249 B2 * | 10/2010 | Saab ............... A61M 25/0009 604/508 |
| 8,285,328 B2 | 10/2012 | Caffey et al. |
| 9,539,389 B2 * | 1/2017 | Trombly ............... A61M 5/172 |
| 2002/0188259 A1 | 12/2002 | Hickle et al. |
| 2002/0193817 A1 | 12/2002 | Lal et al. |
| 2003/0105437 A1 | 6/2003 | Neubert |
| 2003/0236489 A1 * | 12/2003 | Jacobson ............ A61M 5/16886 604/67 |
| 2004/0167464 A1 | 8/2004 | Ireland et al. |
| 2006/0189888 A1 | 8/2006 | Hassler, Jr. et al. |
| 2007/0106247 A1 * | 5/2007 | Burnett ............... A61F 7/12 604/508 |
| 2007/0215545 A1 * | 9/2007 | Bissler ............... A61M 1/16 210/646 |
| 2008/0081631 A1 | 4/2008 | Rofougaran |
| 2008/0129475 A1 * | 6/2008 | Breed ............... G07C 5/008 340/438 |
| 2008/0269678 A1 * | 10/2008 | Rebours ............ A61M 5/16827 604/118 |
| 2008/0306359 A1 * | 12/2008 | Zdeblick ............ A61B 5/0028 600/302 |
| 2009/0198172 A1 | 8/2009 | Garrison et al. |
| 2010/0076366 A1 | 3/2010 | Henderson, Sr. et al. |
| 2010/0114027 A1 | 5/2010 | Jacobson et al. |
| 2010/0198188 A1 | 8/2010 | Heller |
| 2010/0204765 A1 | 8/2010 | Hall et al. |
| 2010/0274221 A1 | 10/2010 | Sigg et al. |
| 2011/0148720 A1 | 6/2011 | Yao et al. |
| 2011/0264033 A1 * | 10/2011 | Jensen ............... A61M 5/1452 604/65 |
| 2011/0275410 A1 * | 11/2011 | Caffey ............ A61M 5/14526 455/557 |
| 2011/0275987 A1 | 11/2011 | Caffey et al. |
| 2012/0185267 A1 * | 7/2012 | Kamen ............... G06Q 50/22 705/2 |
| 2013/0095508 A1 * | 4/2013 | Campitelli ............ B01L 3/0217 435/7.94 |
| 2013/0178826 A1 * | 7/2013 | Li ............... A61M 5/155 604/506 |
| 2013/0204165 A1 * | 8/2013 | Perry ............... A61B 10/0045 600/587 |
| 2014/0107579 A1 | 4/2014 | Lanigan et al. |

* cited by examiner

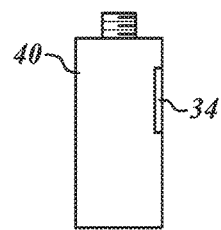
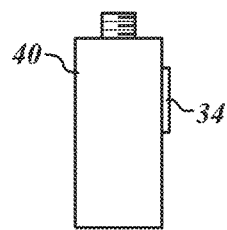
*FIG.4A*          *FIG.4B*
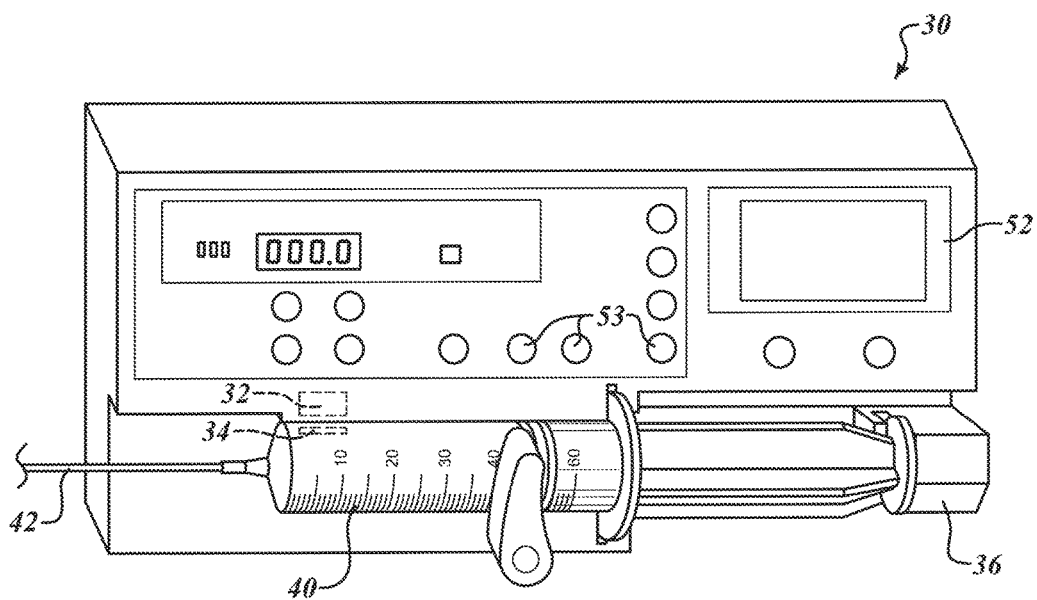
*FIG.5*

WIRELESS STRAIN GAUGE/FLOW SENSOR

CROSS-REFERENCE TO RELATED APPLICATION

This application is a divisional of U.S. application Ser. No. 13/553,541 filed Jul. 19, 2012, now U.S. Pat. No. 9,539,389 and claims the benefit under 35 U.S.C. § 119(e) of U.S. Provisional Patent Application No. 61/596,631 filed Feb. 8, 2012. These applications are incorporated herein by reference in their entirety.

BACKGROUND

Technical Field

The present disclosure relates to integrated sensor devices. The present disclosure relates more particularly to integrated fluid sensors.

Description of the Related Art

Fluid injection systems are utilized in a large variety of applications. Such applications include medical applications, wherein infusion pumps, syringe pumps, auto-injectors, and many other types of devices deliver fluid to a patient. Often, a particular flow rate is desired for delivery of the fluid. For instance, medication or drugs delivered intravenously to a patient during surgery or post-surgery typically are delivered in very precise doses. Delivering an incorrect dose can lead to serious injury or even death. In one common technique for monitoring the flow rate of a drug in an infusion pump, a stepper motor which forces liquid from a reservoir through a feed line to the patient is monitored and displacement of the fluid is calculated based on displacement of the stepper motor. However, such a method for monitoring the flow rate has drawbacks in that it often does not take into account volumetric chamber irregularities, temperature fluctuations, fluid viscosity, atmospheric pressure and back pressure variability. Any error in calculating the flow rate can be very harmful to the patient.

Current infusion pumps, syringe pumps, and auto-injectors lack true closed-loop feedback, like a flow sensor, to ensure that the correct dose size and flow rate are administered for any particular drug. These devices often rely instead on calculations for dose size and flow rate data derived from drip sensors for gravity-based pumps and screw/piston position sensors or load cells used in volumetric pumps. These flow rate and dose size calculation methods are subject to inherent errors introduced by volumetric chamber irregularities, temperature, fluid viscosity, atmospheric pressure, and back pressure variability. Additionally, and perhaps most critically, there is the potentially fatal human error of administering the wrong drug.

BRIEF SUMMARY

In one embodiment, a fluid dispensing system includes a control module and a sensor module. The sensor module is placed in direct contact with the fluid, the fluid flow line, or the fluid container. The sensor module is a wireless sensor module and receives power wirelessly from the control module. The sensor module includes a sensor coupled to an integrated circuit die in which is formed an ASIC. The sensor is formed on a plastic or flex substrate in one embodiment. Alternatively the sensor is a MEMS sensor. The MEMS sensor and the ASIC can be formed in a single integrated circuit die or in separate integrated circuit dies coupled together and packaged in a single package. Each such integrated circuit die, along with any integrated circuit die discussed herein, may be formed in a semiconductor material, and thus may be referred to as a semiconductor integrated circuit die or simply a semiconductor integrated circuit. The sensor module includes an RF antenna which receives RF radiation which is then converted into electric energy which powers the controller and the sensor. The sensor can be a strain gauge, a pressure sensor, a flow rate sensor, or any other suitable sensor capable of measuring a desired fluid parameter.

The control module includes a microcontroller and a transceiver. The transceiver emits radio frequency radiation which is received by the antenna of the sensor module. The transceiver of the control module not only transmits energy via the RF signal, but also data. The sensor module can be placed in contact with a fluid being dispensed. The control module is placed outside of the fluid and outside of a container containing the fluid but in close proximity to the sensor module.

Because the control module is in close proximity to the sensor module, the control module can provide power via RF radiation to the sensor module. Through the MEMS flow rate sensor, the sensor module can take a measurement of the flow rate of the fluid, and the controller can convert the signal from the sensor to a digital signal which can then be output through the antenna to the transceiver of the control module. The control module can be in electrical communication with the fluid dispensing mechanism such as a stepper motor or plunger. In this way, the flow rate can be sensed and controlled in a closed-loop fashion because the sensor module is placed within the fluid dispensing structure. The sensor module is disposable and requires no battery or other power. The sensor module can be inexpensively manufactured and attached within a container that contains the fluid to be dispensed, or within hosiery through which the fluid is dispensed.

BRIEF DESCRIPTION OF THE SEVERAL VIEWS OF THE DRAWINGS

FIG. 4A is a fluid container including a sensor module on an inner wall according to one embodiment.

FIG. 4B is a fluid container including a sensor module on an outer wall according to one embodiment.

FIG. 5 illustrates a syringe pump according to one embodiment.

DETAILED DESCRIPTION

Figure 1A:
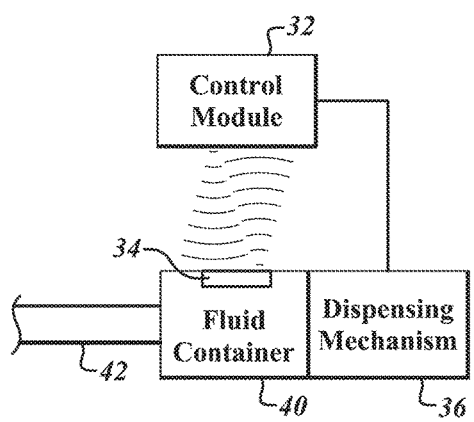
FIG. 1A is a block diagram of a fluid dispensing system including a sensor module coupled on an inside of a fluid container according to one embodiment.

FIG. 1A is a fluid dispensing system 30 according to one embodiment. The fluid dispensing system 30 includes a control module 32 configured to wirelessly communicate with a sensor module 34. A fluid dispensing mechanism 36 is coupled to the control module 32 and to a fluid container 40. The sensor module 34 is coupled inside of the fluid container 40.

The fluid dispensing mechanism 36 receives a command from the control module 32 to dispense fluid from the fluid container 40 through the fluid line 42 at a particular flow rate. The dispensing mechanism 36 then forces fluid from the fluid container 40 through the fluid line 42. The sensor module 34 is positioned within the fluid container 40 to be able to sense a flow rate of the fluid from the fluid container 40, or to sense a parameter of the fluid from which the flow rate of the fluid can be computed. The sensor module 34 does not receive power from a wired connection or from a battery. Instead, the sensor receives power from the control module 32 wirelessly. The control module 32 is coupled to the sensor module 34 by near field communication (NFC). The control module 32 therefore transmits a wireless signal to the sensor module 34. The sensor module 34 receives the signal from the control module and harvests energy from the electric field of the signal. The energy harvested from the wireless signal is the power supply by which the sensor module is powered.

Once the sensor module 34 receives power from the control module 32, the sensor module 34 begins to monitor the flow rate of fluid from the fluid container 40. The sensor module 34 then transmits flow rate data wirelessly to the control module 32. The control module 32 receives the flow rate data and compares the flow rate data to the expected flow rate from the container. If the flow rate data is different than the expected flow rate, then the control module 32 causes the dispensing mechanism 36 to increase or decrease the flow of fluid from the fluid container 40 as the case may be. The control module 32 can also cause the dispensing mechanism to cease delivery of the fluid according to flow rate data.

If the flow rate data received from the sensor module 34 agrees with the expected flow rate within an acceptable tolerance range, then the control module 32 does not cause the fluid dispenser 36 to adjust the flow of fluid from the fluid container 40. In this way a feedback loop is established to continuously monitor and adjust the flow rate of the fluid from the fluid container 40.

The fluid dispensing system 30 of FIG. 1A does not suffer from the drawbacks of many previous systems. The sensor module 34 can be placed directly in contact with the fluid within the fluid container 40 or the fluid line 42 because the sensor module is wireless and battery-less. In many sensitive fluid dispensing systems 30, a sensor module 34 containing a battery cannot be placed directly in the fluid due to the risk of chemicals leaking from the battery.

Figure 1B:
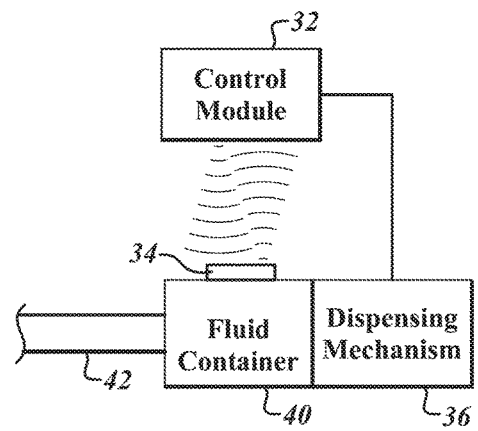
FIG. 1B is a block diagram of a fluid dispensing system including a sensor module coupled on an outside of a fluid container according to one embodiment.
Figure 1C:
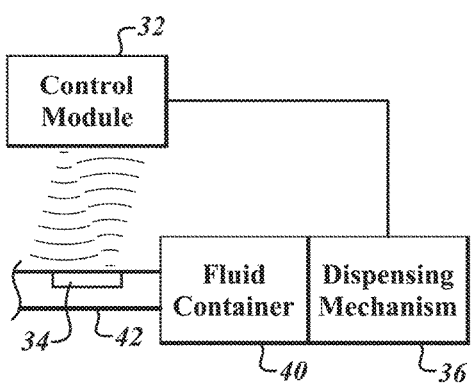
FIG. 1C is a block diagram of a fluid line system including a sensor module coupled on an inside of a fluid container according to one embodiment.
Figure 1D:
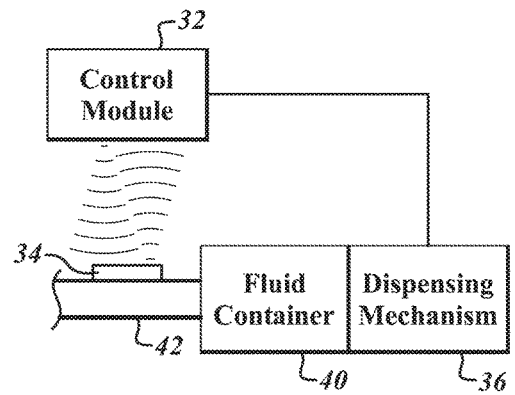
FIG. 1D is a block diagram of a fluid line system including a sensor module coupled on an outside of a fluid container according to one embodiment.

FIG. 1B is a block diagram of a fluid dispensing system 30 according to one embodiment. In FIG. 1B the sensor module 34 is coupled to an outside of the fluid container 40. In this configuration the sensor module can detect the flow rate by detecting a strain or deformation in the surface of the fluid container 40. The sensor module 34 can also be placed in the fluid line 42 as shown in FIG. 1C, or on an outer surface of the fluid line 42 as shown in FIG. 1D. Alternatively the sensor module 34 can be placed at a junction of fluid lines on or within a connection structure connecting two fluid lines 42 or a fluid line 42 and a needle, or a fluid line 42 and the fluid container 40. The sensor module 34 detects the flow rate of the fluid directly, or indirectly by detecting pressure, strain, capacitance, or any other suitable fluid parameter from which a measure of the flow rate can be obtained.

Figure 2:
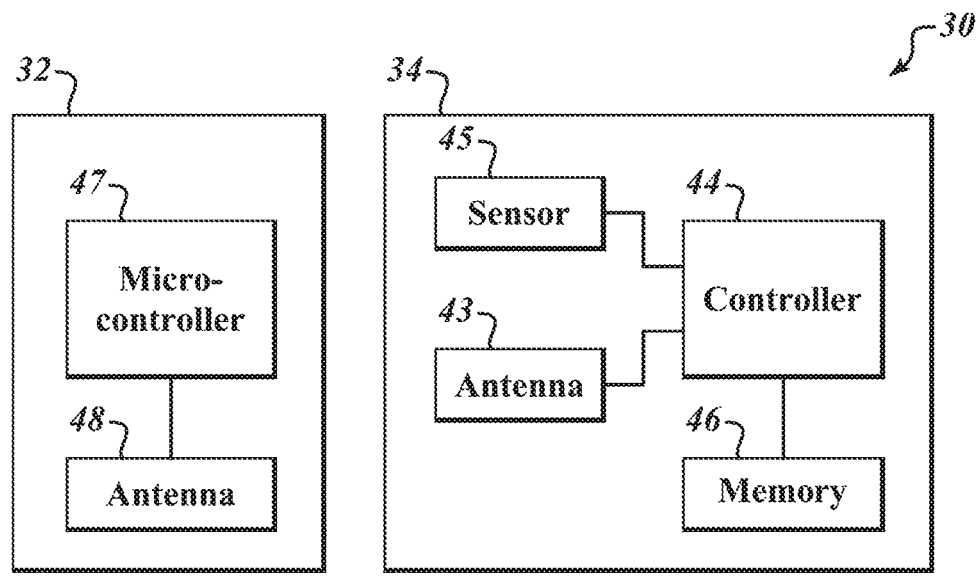
FIG. 2 is a block diagram of a fluid dispensing system according to an alternate embodiment.

FIG. 2 illustrates a fluid dispensing system 30 according to one embodiment. The fluid dispensing system 30 includes a control module 32 and a sensor module 34. The sensor module 34 includes an antenna 43 coupled to a microcontroller 44. A sensor 45 and a memory 46 are also coupled to the microcontroller 44. The control module 32 includes a microcontroller 47 and an antenna 48.

As described previously, the sensor module 34 is a wireless sensor module. It does not receive power from a battery or from a wired connection. Rather, the sensor module 34 can be placed within the fluid because it receives power wirelessly from the antenna 48 of the control module 32. In particular, the microcontroller 47 modulates the antenna 48 to emit radiation in the RF spectrum according to known near field coupling transmission protocols. The antenna 43 of the sensor module 34 receives the RF radiation from the antenna 48 and transmits the signal to the microcontroller 44 which harvests energy from the radiation received by the antenna 43. The energy harvested by the microcontroller 44 is used to power the microcontroller 44, the memory 46, the sensor 45, and the antenna 43 of the sensor module 34.

The microcontroller 44 receives fluid data from the sensor 45 and converts it from an analog signal to a digital signal. The microcontroller 44 modulates the antenna 43 to transmit the digital sensing data to the antenna 48. The microcontroller 47 receives the digital sensing data from the antenna 48. Upon receiving the digital sensing data from the antenna 48, the microcontroller 47 can regulate the dispensing mechanism 36 accordingly. If the microcontroller 47 receives the flow rate data and determines that the flow rate of the fluid is too high or too low, then the microcontroller 47 can control the dispensing mechanism 36 to appropriately adjust the flow of the fluid.

A fluid dispensing system 30 according to FIG. 2 is particularly useful in the medical fields, in which specific drugs must be dispensed at a specific rate to a patient. However, the fluid dispensing system 30 can be used in any other suitable fluid dispensing configuration. For example, the fluid dispensing system 30 can be used to dispense fuel in a machine, lubricant to lubricate parts of a machine, chemicals in a reaction or deposition chamber, or any other suitable fluid dispensing system. The fluid dispensing system 30 can therefore be a medical fluid dispensing system, an automotive fluid dispensing system, a mechanical fluid dispensing system, an environment fluid dispensing system, an experimental fluid dispensing system, or any other system in which fluid is dispensed at a controlled rate.

Figure 3:
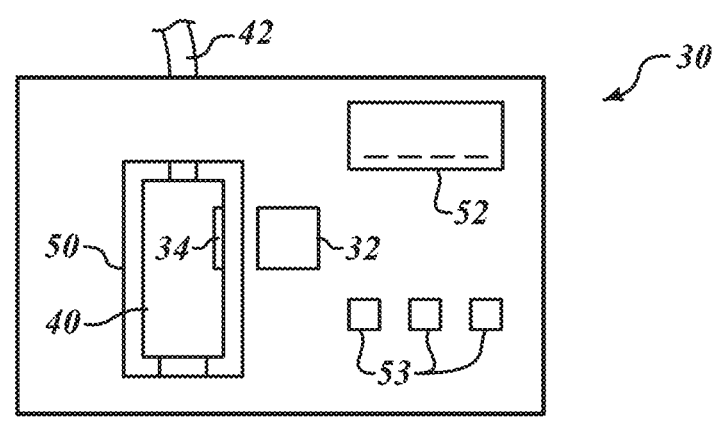
FIG. 3 illustrates a fluid dispensing system according to one embodiment.

FIG. 3 illustrates a fluid dispensing system 30 according to one embodiment. In one configuration, the fluid dispensing system 30 of FIG. 3 includes a replaceable fluid container 40 placed within a container slot 50 of the fluid dispensing system 30. When placed within the container slot 50 of the fluid dispensing system 30, the fluid container 40 is in connection with the fluid line 42. The fluid dispensing system 30, utilizing a dispensing mechanism 37 such as a stepper motor and piston arrangement, then causes fluid to flow from the fluid container 40 through the fluid line 42 to a patient receiving medical treatment. Conveniently, a sensor module 34 is placed within the fluid container 40. The fluid container 40 is installed in the container slot 50 in such a manner that the sensor module 34 is adjacent a control module 32 of the fluid dispensing system 30. Because the sensor module 34 is in close proximity to the control module 32, the control module 32 can transmit RF radiation to the sensor module 34, as described previously. The sensor module 34 then harvests energy from the RF radiation transmitted by the control module 32. Being thus powered by the control module 32, wirelessly, the sensor module 34 senses the flow rate of the fluid within the fluid container 40. The sensor module 34 then transmits the flow rate data to the control module 32. The control module 32 processes the flow rate data and determines whether the flow rate is too high, too low, or in a proper state.

The fluid dispensing system 30 also contains a display 52 and inputs 53. The display 52 can display the current flow rate of the fluid so that a technician standing by can monitor the flow rate. The fluid dispensing system 30 can also transmit in a wired manner or in a wireless manner the flow rate data to a central database, a remote monitor where another technician can view it, or to any other suitable location which can then monitor the flow rate. If the control module 32 determines that a malfunction has occurred or that there is a dangerous flow rate, an alert can be signaled both on the display 52 or at a remote monitoring station or computer. Additionally, a technician standing by can operate inputs 53 to inhibit further dispensation of the fluid, to slow down or to speed up the flow rate, or to perform any other useful or suitable function.

In one embodiment, the fluid container 40 and the sensor module 34 are both disposable. Thus, after the fluid has been dispensed from the fluid container 40, the fluid container 40 is removed from the container slot 50 and disposed of properly. A new fluid container 40 with a sensor module 34 can be placed in the container slot 50 so that further fluid can be dispensed therefrom.

The sensor module 34 also includes a memory 46 as described previously. The memory 46 can store data regarding the type of fluid container 40 that the sensor module 34 is placed in, historical data regarding past flow rates, software instructions for operation of the sensor module, or any other suitable information. For example, the sensor module 34 can store data identifying a particular type of fluid container 40 as well as the specific fluid within the fluid container 40. Thus, when the fluid container 40 is placed within the container slot 50, the control module 32 begins to transmit RF radiation, thereby powering on the sensor module 34. The sensor module 34 thus receiving power then transmits to the control module 32 data regarding the drug within the fluid container 40. Therefore in one example the sensor module 34 transmits to the control module 32 that it is in an insulin fluid container 40. The control module 32 can therefore determine whether the proper fluid container 40 is installed in the container slot 50. If the control module 32 determines that the incorrect drug container is placed within the container slot 50, then the control module 32 can prohibit the fluid dispensing system 30 from dispensing the fluid. The display 52 can then display that the wrong fluid is within the container slot 50. This configuration enhances the safety of the fluid dispensing device 30 and can save patients from severe injury or even death.

FIG. 4A illustrates a disposable fluid container 40 according to one embodiment. The disposable fluid container 40 as illustrated in FIG. 4A has not been placed within a fluid dispensing system 30. The fluid container 40 includes a sensor module 34 configured to sense the flow rate of a fluid leaving the fluid container 40. FIG. 4B illustrates a drug container according to an alternative embodiment. In FIG. 4B, the sensor module 34 is placed on an outer wall of the fluid container 40. The sensing device of the sensor module 34 is configured not to interact directly with the fluid within the fluid container 40, but rather to measure the pressure of the walls of the fluid container 40. From this measurement an indication of the flow rate can be obtained. For example, if a strain gauge or a pressure sensor of the sensor module 34 detects that the walls of the fluid container 40 have expanded slightly, this can indicate that the stepper motor of the fluid dispensing system 30 has begun to expel fluid from the fluid container 40. When this happens, a slight increase in pressure can be experienced on the walls of the fluid container 40. A very accurate analysis of the flow rate of the drug from the fluid container 40 can be obtained in this manner.

In one embodiment, the fluid container 40 is made of a plastic material which expands in a known manner under pressure. Alternatively, the sensor module 34 can be embedded within the walls of the fluid container 40. Many other suitable configurations of the sensor module 34 within or on the fluid container 40 are possible. All such configurations fall within the scope of the present disclosure.

FIG. 5 illustrates a syringe pump 30 according to one embodiment. Syringe pumps are used in medical applications in which a patient is to receive a specific dose of medication over a specific period of time. Thus the medication is to be dispensed at a particular average flow rate. The syringe pump 30 includes a fluid chamber 40 from which the medication is dispensed. A dispensing mechanism 36 is coupled to a piston which drives fluid from the fluid chamber 40. A sensor module 34 is placed on the fluid chamber 40 to measure a flow rate of the fluid from the fluid chamber 40. A control module 32 is placed on the syringe pump adjacent to the sensor module 34. The syringe pump 30 further includes a display 52 and a user input 53.

When a patient is to receive medication from the syringe pump, the syringe is placed in the syringe pump 30 such that the sensor module 34, which is attached to the fluid chamber 40 of the syringe, is adjacent the control module 32. The sensor module 34 and the control module 32 are positioned sufficiently close to each other to allow NFC between them. In one embodiment the sensor module 34 is spaced about 5 mm or less from the control module 32. The maximum spacing of the sensor module 34 and the control module 32 is based in part on the constraints of NFC technology and the particular components of the control module 32 and the sensor module 34.

A fluid line 42 is coupled between the fluid chamber 40 and the patient, terminating in a needle or IV coupled to the patient. A medical technician then enters instructions into the input 53 of the syringe pump 30. The control module 32 stores data from the input 53 regarding the desired time period and flow rate for the dispensation of the fluid. The control module 32 then causes the dispensing mechanism 36, a stepper motor in one example, to begin to drive fluid from the fluid chamber 40 through the fluid line 42. The control module 32 also initiates NFC with the sensor module 34. The sensor module 34 harvests energy from the wireless transmissions of the control module 32 and begins to monitor a flow rate of the fluid from the fluid chamber 40. The sensor module 34 transmits flow rate data to the control module 32. The control module 32 then causes the dispensing mechanism 36 to adjust the flow rate of the fluid according to the flow rate data received from the sensor module 34.

Figure 6:
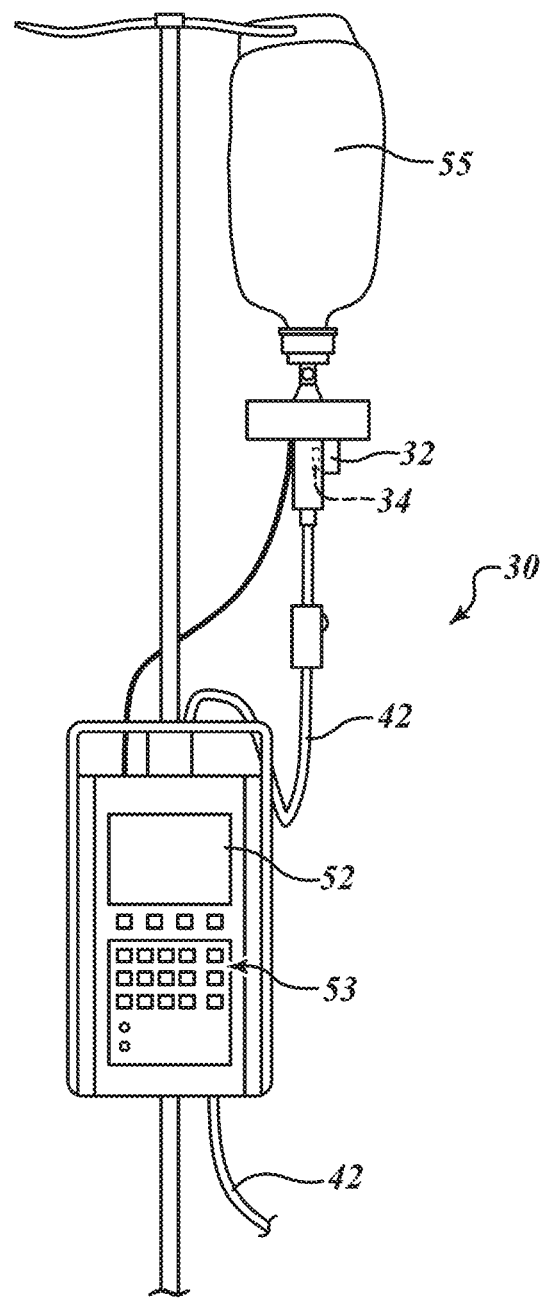
FIG. 6 illustrates an infusion pump according to one embodiment.

FIG. 6 illustrates an infusion pump 30 according to one embodiment. The infusion pump 30 includes an IV bag coupled to a drip chamber 40. The drip chamber 40 is further coupled to a fluid line 42 which delivers medication from the IV bag to a patient. The infusion pump includes a display 52 and a user input 53. A sensor module 34 is attached to the drip chamber 40. A control module 32 is coupled to a clip adjacent the sensor module 34 to enable NFC between the sensor module 34 and the control module 32 as described previously. The control module 32 is coupled to the infusion pump by a wired connection or by a wireless connection.

When a patient is to receive fluid from the infusion pump 30, the IV bag is placed in the infusion pump 30 such that the sensor module 34, which is attached to the drip chamber 40 of the infusion pump, is adjacent the control module 32. The sensor module 34 and the control module 32 are positioned sufficiently close to each other to allow NFC between them. In one embodiment the sensor module 34 is spaced about 5 mm or less from the control module 32. The maximum spacing of the sensor module 34 and the control module 32 is based in part on the constraints of NFC technology and the particular components of the control module 32 and the sensor module 34.

A fluid line 42 is coupled between the drip chamber 40 and the patient, terminating in a needle or IV coupled to the patient. A medical technician then enters instructions into the input 53 of the infusion pump 30. The control module 32 stores data from the input 53 regarding the desired time period and flow rate for the dispensation of the fluid. The control module 32 then causes the dispensing mechanism 36 to begin to drive fluid from the fluid chamber 40 through the fluid line 42. The control module 32 also initiates NFC with the sensor module 34. The sensor module 34 harvests energy from the wireless transmissions of the control module 32 and begins to monitor a flow rate of the fluid from the fluid chamber 40. The sensor module 34 transmits flow rate data to the control module 32. The control module 32 then causes the dispensing mechanism 36 to adjust the flow rate of the fluid according to the flow rate data received from the sensor module 34.

Figure 7:
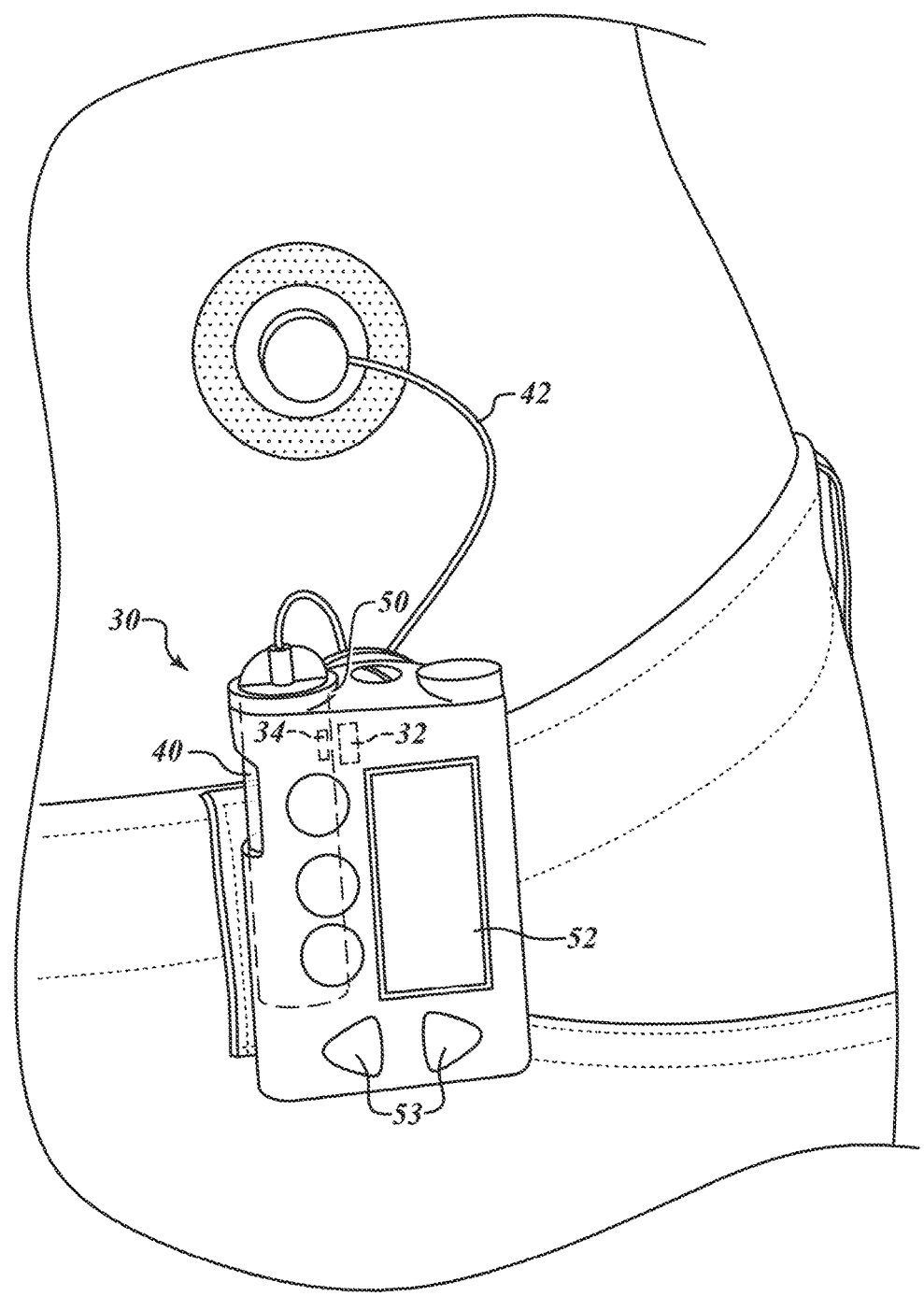
FIG. 7 illustrates an insulin pump according to one embodiment.

FIG. 7 illustrates a portable insulin pump 30 according to one embodiment. The insulin pump 30 is connected to a belt at the waist of a patient. The insulin pump 30 is configured to deliver insulin in a controlled manner to the patent. The insulin pump 30 includes a replaceable insulin cartridge 40 placed in a cartridge port 50 of the insulin pump 30. The insulin cartridge 40 is further coupled to a fluid line 42 which delivers insulin from the insulin cartridge to a patient. The insulin pump 30 includes a display 52 and a user input 53. A sensor module 34 is attached to the insulin cartridge 40. The insulin pump 30 further includes a control module 32 positioned so that when the replaceable insulin cartridge 40 is placed within the insulin pump 30, the control module 32 is adjacent the sensor module 34 of the insulin cartridge 30 to enable NFC between the sensor module 34 and the control module 32 as described previously. The control module 32 is coupled to the infusion pump by a wired connection or by a wireless connection.

When a patient is to receive fluid from the insulin pump 30, the insulin cartridge 40 is placed in the insulin pump 30. The cartridge 40 and port 50 are shaped such that installing the cartridge 40 in the port 50 places the sensor module 34 in close proximity to the control module 32. The sensor module 34 and the control module 32 are positioned sufficiently close to each other to allow NFC between them. The patient then enters input commands to the user input 53. The control module 32 causes a dispensing mechanism 36 within the insulin pump 30 to begin dispensing insulin from the insulin cartridge 40. The insulin flows from the insulin cartridge 40 through the fluid line 42 and into the patient. A medical technician then enters instructions into the input 53 of the infusion pump 30. The control module 32 also initiates NFC with the sensor module 34. The sensor module 34 harvests energy from the wireless transmissions of the control module 32 and begins to monitor a flow rate of the insulin from the insulin cartridge 40. The sensor module 34 transmits flow rate data to the control module 32. The control module 32 then causes the dispensing mechanism 36 to adjust the flow rate of the insulin according to the flow rate data received from the sensor module 34.

Figure 8:
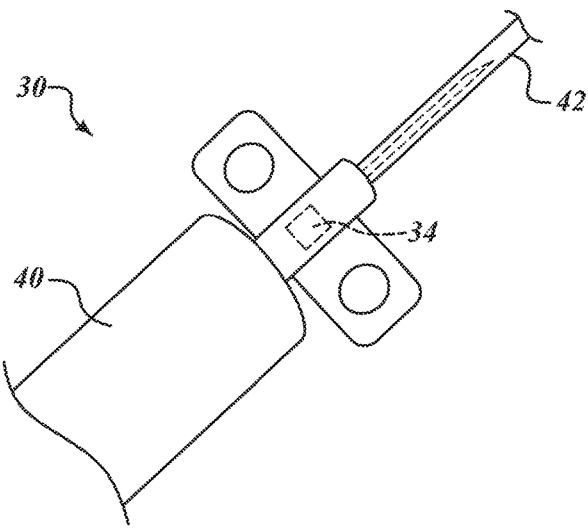
FIG. 8 illustrates an intravenous fluid delivery system according to one embodiment.

FIG. 8 illustrates fluid dispensing system 30 according to one embodiment. The fluid dispensing system 30 includes a syringe 40, an IV connector 51, and a fluid line 42. The IV connector 51 connects the syringe 40 to the fluid line 42. A sensor module 34 is placed within the IV connector 51. A control module 32, not pictured in FIG. 8, can be coupled to the outside of the IV connector 51 at an appropriate distance to be able to initiate NFC with the sensor module 34 as described previously. The control module 32 is connected to a dispensing mechanism that forces fluid from the syringe 40, through the IV connector and fluid line 42 to a patient. As described previously, the control module 32 also initiates NFC with the sensor module 34. The sensor module 34 harvests energy from the wireless transmissions of the control module 32 and begins to monitor a flow rate of the fluid from the syringe 40. The sensor module transmits flow rate data to the control module 32. The control module 32 then causes the dispensing mechanism 36 to adjust the flow rate of the fluid according to the flow rate data received from the sensor module 34.

While the sensor has been depicted in various positions attached to various components of fluid dispensing systems 30, the sensor module 34 can be placed in any suitable position. The sensor module 34 can be small enough to fit within very small fluid lines and structures. The sensor module 34 can be on the outside or the inside of the various structures. The sensor module 34 can even be placed within the wall of a fluid line 42 or fluid chamber 40.

Figure 9:
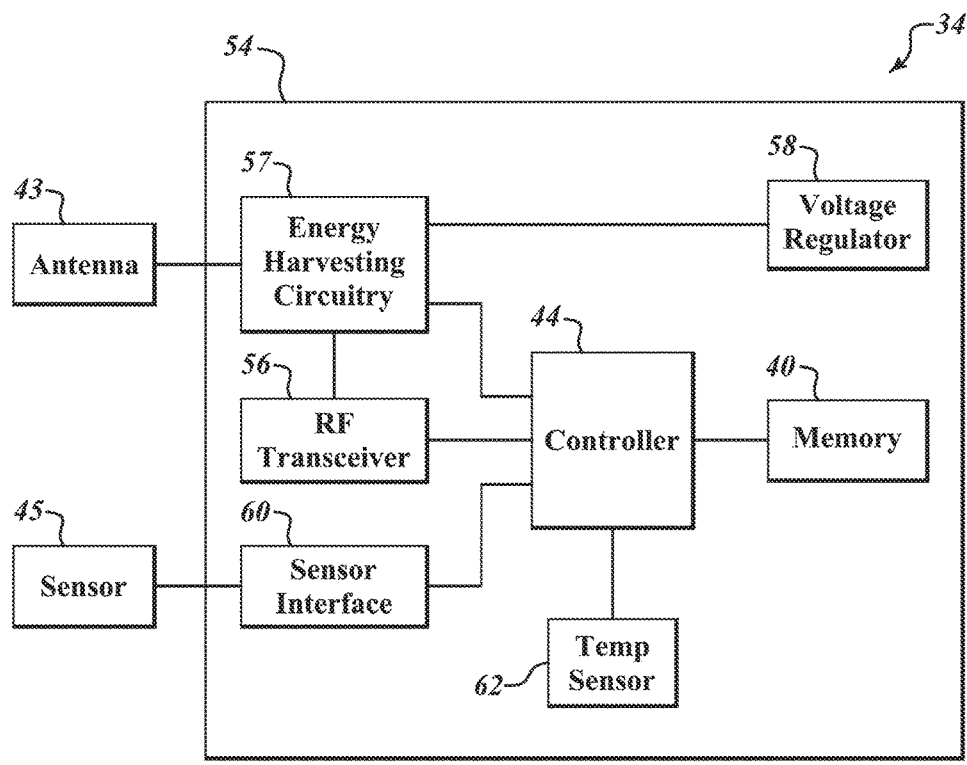
FIG. 9 is a block diagram of a sensor module according to one embodiment.

FIG. 9 illustrates a sensor module 34 according to one embodiment. The sensor module 34 includes an antenna 43 and a sensor 45 coupled to an ASIC 54. In particular the antenna 43 is coupled to energy harvesting circuitry 57 of the ASIC. The energy harvesting circuitry can include rectifier and clock circuitry which performs a function of harvesting energy from the radiation received by the antenna 43. The energy harvesting circuitry 57 is further coupled to a voltage regulator 58. The voltage regulator 58 regulates the voltage generated by harvesting energy from the antenna 43. The voltage regulator 58 can also include power-on reset functionality. An RF transceiver 56 is coupled to the antenna circuitry 43 through the energy harvesting circuitry 57. The RF transceiver 56 is also coupled to a controller 44. The sensor 45 is coupled to the controller 44 through a sensor interface 60. A memory 46 and a temperature sensor 62 are also coupled to the controller 44.

The controller 44 modulates the RF transceiver 56 so that the RF transceiver 56 can transmit, through the antenna 43, signals relating to sensor data, as described previously. The controller 44 can also receive digital signals from the control module 32 through the antenna 43 and the RF transceiver 56.

The sensor module 34 is configured to be coupled to a control module 32 by NFC. In particular, the antenna 43 receives wireless signals from the control module 32. The energy harvesting circuitry 56 harvests energy from the wireless signals in a known manner. The voltage regulator 58 regulates the voltage generated from the wireless signals to provide a steady voltage supply to the rest of the components of the sensor module 34. When the sensor module 34 is being powered by the control module 32, the sensor 45 senses the flow rate or other suitable parameter of the fluid in which it is placed. The sensor 45 passes a sensor signal to the sensor interface circuitry 60 which passes the signal to the controller 44. The controller 44 processes the sensor signal. In one embodiment the controller 44 includes analog to digital conversion circuitry to convert the sensor signal to a digital sensor signal. The controller 44 then causes the transceiver 57 to modulate the antenna 43 to transmit the digital sensor data to the control module 32. The controller 44 can store sensor data in the memory 46. The memory 46 can also contain software instructions for operation of the sensor module 34. The memory 46 can also include fluid identification data which identifies the type of fluid in a fluid container 40 in which the sensor module 34 is to be placed. The controller 44 can transmit the fluid identification data to the control module 32.

The temperature sensor 62 can be utilized to further increase the accuracy of the flow rate data gathered by the controller 44. In particular, pressure and strain and capacitance measurements of the sensor 45 can vary according to the temperature. In order to control for the effects of temperature variation, the controller 44 receives a temperature measurement from the temperature sensor 62. The temperature sensor 62 can be a bandgap sensor or any other suitable sensor. The controller 44 receives sensor data from the sensor 45. The controller 44 calculates a flow rate or a pressure or strain, or any other suitable parameter, based on signals received from the sensor 45. The controller 44 can take into account the temperature data received from the temperature sensor 62 and compute or estimate an accurate determination of the flow rate or other desired parameter, and output such data to the RF transceiver 56, which then transmits the data through the antenna 43. The particular configuration shown in FIG. 9 is given only by way of example. Many other components can be used and other configurations of the components shown can also be made. Such other configurations and components fall within the scope of the present disclosure.

Figure 10A:
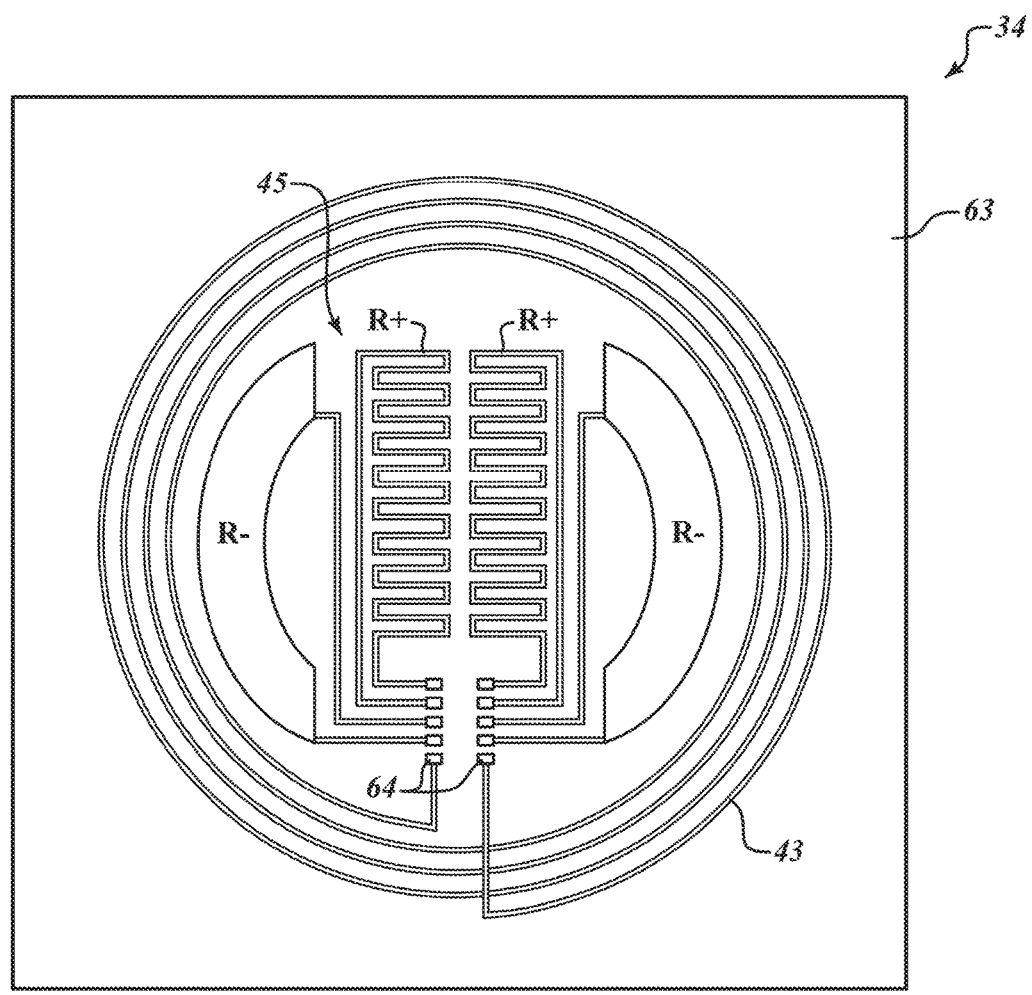
FIG. 10A illustrates a sensor module prior to attachment according to one embodiment.

FIG. 10A illustrates a sensor module 34 according to one embodiment. The sensor module 34 includes a coil antenna 43 positioned on a substrate 63. A strain gauge 45 is also positioned on the substrate 63. The strain gauge includes two resistors R+ and two resistors R−. The resistors are for example piezo electric resistors having resistances that change under stress or strain. Ten electrical contacts 64 are positioned on the substrate 63. The resistors R+, R− and the antenna coil 43 are coupled between the contacts 64. The contacts 64 are configured to connect an ASIC 54 to the antenna coils 43 and the resistors R+, R−.

Figure 10B:
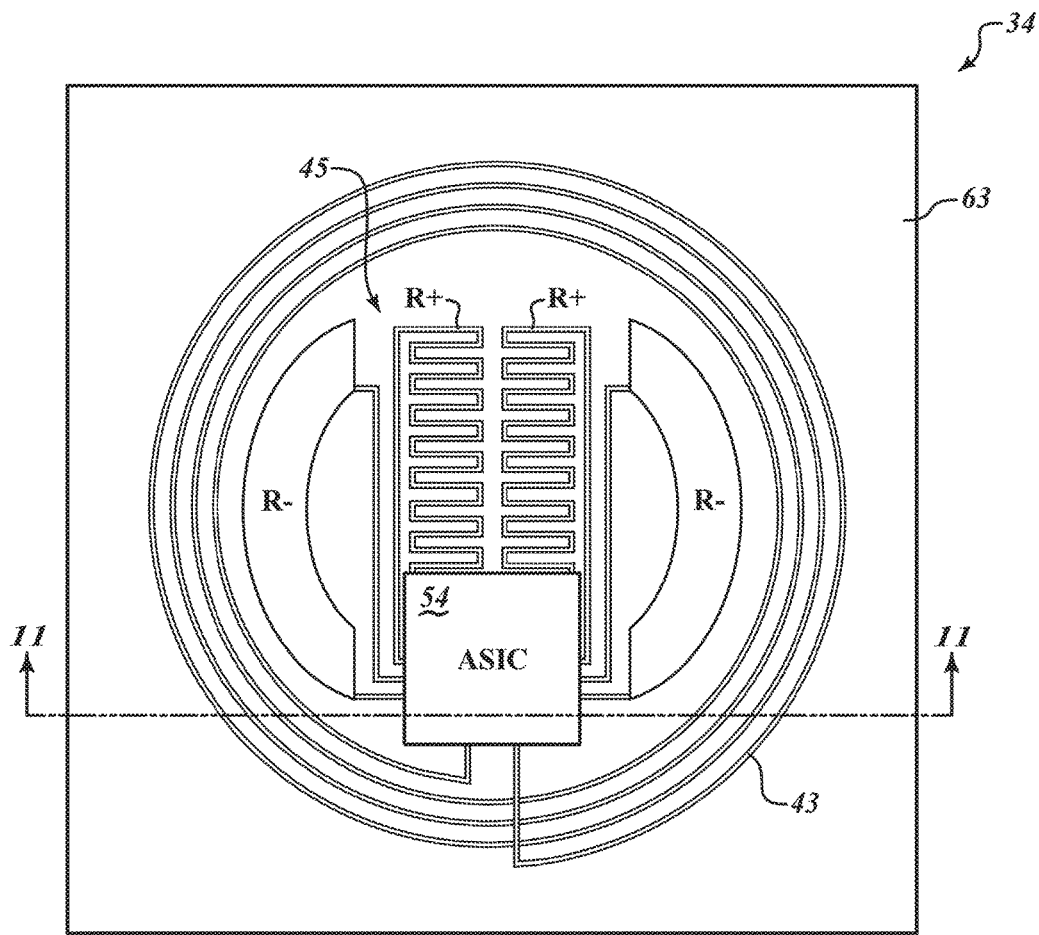
FIG. 10B illustrates a sensor module after attachment of an ASIC according to one embodiment.

In FIG. 10B an ASIC 54 has been placed on the substrate 63 in contact with the electrical contacts 64. When the ASIC 54 is electrically connected to the contacts 64, the four resistors R+, R− are connected in a bridge configuration. The ASIC 54 can monitor the resistances of the resistors R+, R−. By monitoring the resistances of the resistors 64, a measurement of strain in the resistors R+, R− can be obtained. From the strain measurement, the flow rate of a fluid can be obtained.

The sensor module 34 of FIG. 10B can be implemented in a silicon-on-plastic configuration. The antenna coil 43 and the strain gauge 45 can be formed on a plastic or flex substrate 63. The ASIC 54 is also placed on the plastic or flex substrate 63. Contacts 64 electrically connect the antenna coil 43 and the strain gauge 45 to the ASIC 54. The antenna 43 and the strain gauge 45 can be formed by printing metal and piezo-resistive materials onto the substrate 63 or in any other suitable manner. Methods and structures for implementing NFC antennas are well known in the art and are not detailed here. Some examples of how to implement an antenna 43 are shown in US Patent Application No. 2011/0148720 and 2008/0081631 which are hereby incorporated by reference. Methods and structures for forming strain gauges are likewise well known in the art and are not detailed here. For example, it is well known that strain gauges can be formed using piezoresistive resistor bridges, optical strain gauges, and many other suitable methods and structures. One example of a strain gauge is given in US Patent Application No. 2007/0240524 which is incorporated herein by reference.

The antenna 43 is energized when it receives radiation from an antenna 48 of a control module 32. The radiation is in the radio frequency spectrum and the ASIC 54 contains circuitry which harvests energy from the radiation received by the antenna 43. The ASIC 54 is thus powered by the antenna 43. The ASIC 54 can then monitor the strain gauge 45 by which flow rate or other fluid parameters can be measured. The ASIC 54, after ascertaining the flow rate, then modulates the antenna 43 to transmit the flow rate data or other suitable sensor data to the antenna 48 of the control module 32 as described previously. In an alternative embodiment, RF transceiver 56 and energy harvesting circuitry 57 can be formed on separate substrates or in separate integrated circuit dice on the substrate 63 and coupled to the ASIC 54.

In one embodiment the antenna 43 is coupled to the ASIC such that the metal of the antenna is between the ASIC and the plastic or flex substrate. The metal of the strain gauge is not in contact with the fluid. But rather, the plastic or flex substrate is in contact with the fluid and deforms according to the strain or pressure in the fluid and thereby causes the printed metal of the strain gauge to deform as well. This deformation of the strain gauge changes the resistance of the strain gauge. The ASIC therefore monitors the resistance of the strain gauge, or strain gauges in a bridge formation, and can calculate strain, pressure, flow rate, or any other suitable parameters to be measured based on this change in resistances of the resistors R+, R− of the strain gauge or strain gauges.

Figure 11:
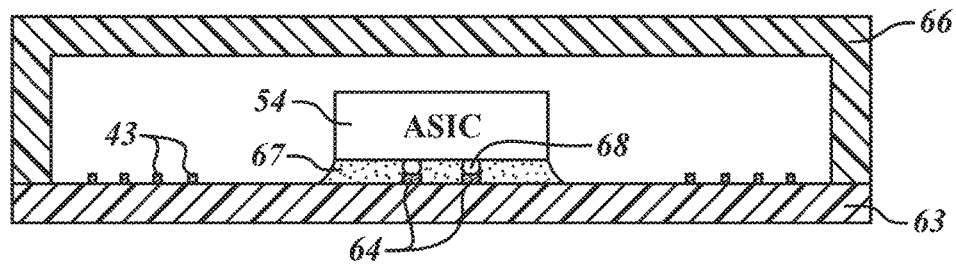
FIG. 11 is a cross section of a sensor module according to one embodiment.

FIG. 11 is a cross section of the sensor module 34 taken along section lines 11 of FIG. 10B according to one embodiment. The ASIC 54 is coupled to the substrate 63 by an adhesive underfill 67. The ASIC 54 is electrically coupled to the contacts 64 by solder balls 68. The sensor module 34 includes a cap 66 placed on the substrate 63. The cap 66 is configured to seal the ASIC, stain gauge 45, and antenna 43 in a protected cavity defined by the cap 66 and the substrate 63. The ASIC 54, antenna 43, and strain gauge 45 are thereby protected from contamination by the fluid in which the sensor module is placed or from other environmental contaminants as well as physical damage.

In FIG. 11, the antenna coil 43 is visible on the substrate 63 as well as two contacts 64 coupled to the antenna coil 43. The strain gauge 45 is not visible in FIG. 11. The sensor module 34 is configured to be placed within a fluid to be monitored, or on a surface of a fluid line 42 or fluid container 40.

The sensor module 34 of FIG. 11 is given only by way of example. Alternative configurations are possible as will be apparent to those of skill in the art in light of the present disclosure. In particular, the strain gauge 45, the antenna coil 43, and the ASIC 54 can be placed on different surfaces and in different configurations. Other types of sensors can be used instead of a strain gauge 45.

Figure 12:
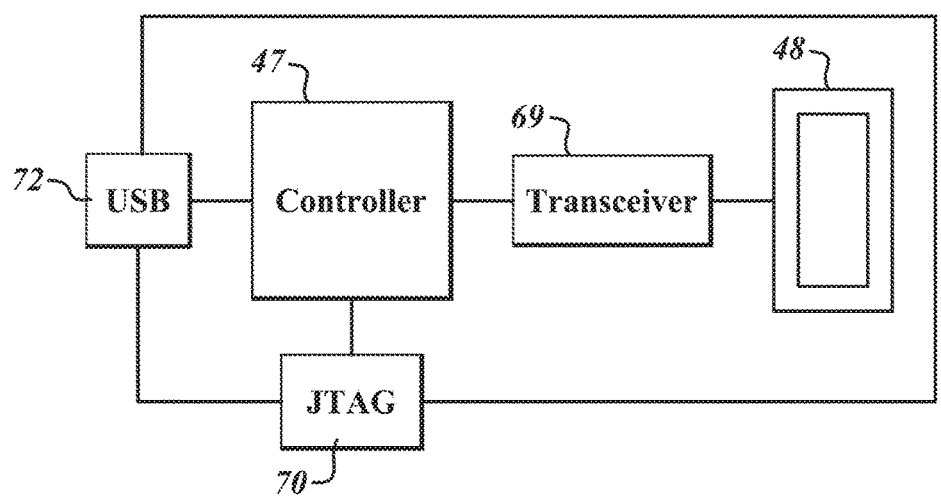
FIG. 12 is a block diagram of a sensor module according to one embodiment.

FIG. 12 illustrates a control module 32 according to one embodiment. The control module 32 includes a transceiver 69 coupled to a microcontroller 47 and an antenna 48. A USB port 72 is coupled to the microcontroller 47. A JTAG port is also coupled to the microcontroller 47.

The microcontroller 47 controls the antenna 48 and thereby causes the antenna 48 to radiate RF radiation to power a sensor module 34 which is adjacent the control module 32. The antenna 48 transmits data and interrogation signals to the sensor module 34 and receives data from the sensor module 34. The antenna 48 supplies the data received from the sensor module 34 to the microcontroller 47. The microcontroller 47 can then control the fluid dispensing mechanism 36 of a fluid dispensing system 30.

The USB port 72 and the JTAG port 70 can be utilized to program the control module 32, debug the control module 32, and receive data from the control module 32. The control module 32 of FIG. 12 can be packaged in an integrated circuit package and installed in a fluid dispensing system 30 adjacent a sensor module 34 as described previously.

Figure 13:
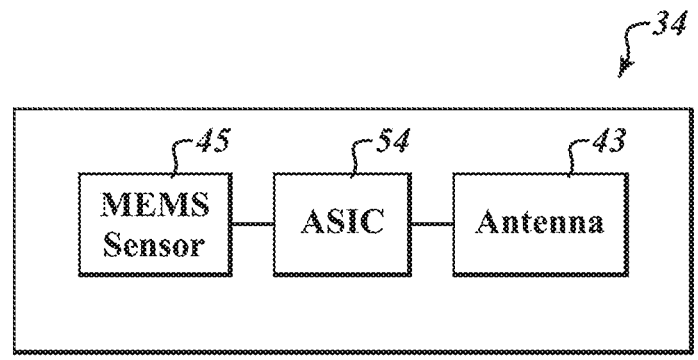
FIG. 13 is a block diagram of a sensor module including a MEMS sensor and an ASIC according to one embodiment.

FIG. 13 is a block diagram of a sensor module 34 according to one embodiment. The sensor module 34 includes an antenna 43 coupled to an ASIC 54. The ASIC 54 is further coupled to a MEMS fluid sensor 45.

As described previously, the sensor module 34 is placed in a fluid container or in a fluid channel such as a drug cartridge or IV line. The sensor module 34 is adjacent a control module 32. The antenna 43 receives electromagnetic radiation from the control module 32. The ASIC 54 includes energy harvesting circuitry which harvests energy from the radiation received by the antenna 43. The ASIC 54 also includes transceiver circuitry for operating the antenna 43. The ASIC 54 is powered by the energy harvested from the radiation received by the antenna 43. The MEMS sensor 45 detects a parameter of the fluid, such as a flow rate, a pressure, or other suitable parameter. The ASIC 54 receives a sensor signal from the sensor 45 indicative of the fluid parameter. The ASIC 54 then modulates the antenna 43 to transmit fluid data to the control module 32.

Figure 14:
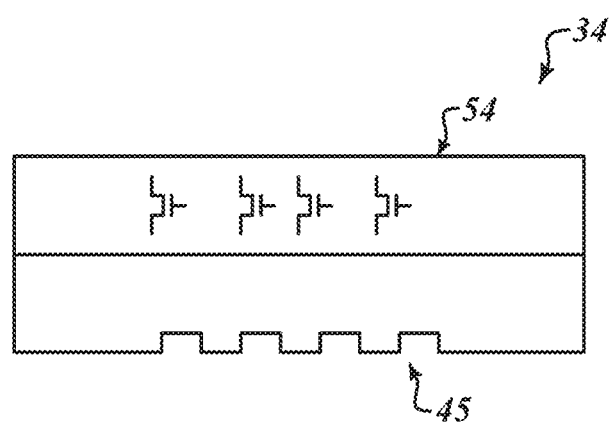
FIG. 14 is a cross section of a sensor module including a MEMS sensor according to one embodiment.

FIG. 14 is a simplified cross section of a control module 32 according to one embodiment. The sensor module 34 includes an ASIC 54 formed in a first substrate and a MEMS sensor 54 formed in a second substrate and coupled to the first substrate. The sensor module 54 of FIG. 3 can be encapsulated in an integrated circuit package suitable for being placed in a fluid. The packaging can include inlets to allow fluid to contact the MEMS sensor 54.

Figure 15:
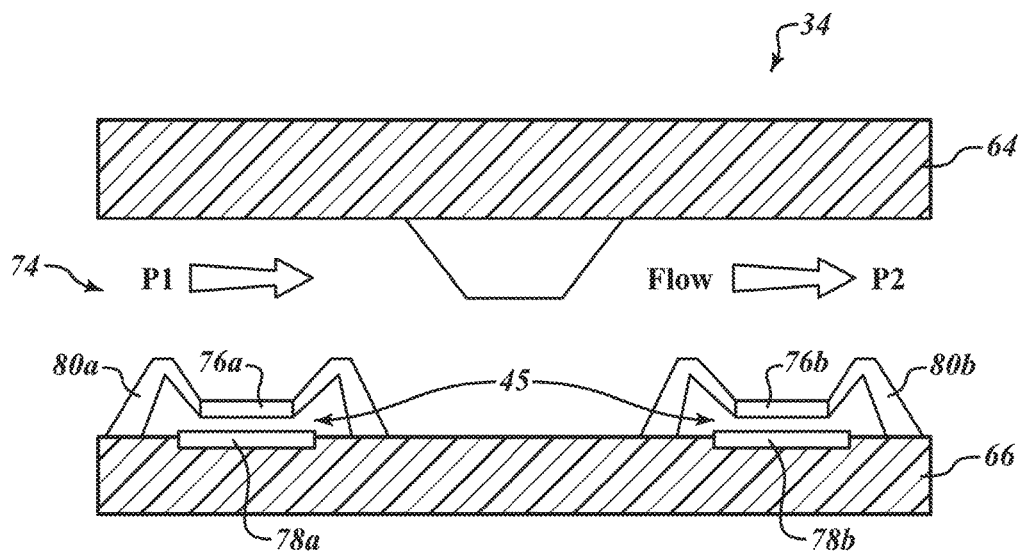
FIG. 15 is a cross section of a fluid sensor according to one embodiment.

FIG. 15 is a cross section of a sensor module 34 according to one embodiment. The sensor module 34 includes a fluid channel 74 defined between a first substrate 64 and a second substrate 66. Two capacitive fluid sensors 45 are placed within the channel 74. Each capacitive fluid sensor 45 includes a respective top capacitor plate 76a, 76b and a respective bottom capacitor plate 78a, 78b. The top capacitor plates 76a, 76b are coupled to respective flexible members 80a, 80b which allow the top capacitor plates 76a, 76b of each capacitive fluid sensor 45 to deflect nearer to or further from the respective bottom capacitor plates 78a, 78b of the capacitive fluid sensors 45.

When the sensor module 34 is placed in a flowing fluid, fluid flows through the channel 74. The pressure of the fluid in the channel is influenced by the flow rate of the fluid through the channel. As the pressure in the channel 74 decreases, the top capacitor plates 76a, 76b of the capacitive fluid sensors 45 deflect further from the bottom capacitor plates 78a, 78b and the capacitance between the plates decreases, thereby giving an indication of the pressure and the flow rate in the channel 74. In some circumstances the fluid may have a first pressure P1 at the entrance of the channel 74 and a second pressure P2, which can be taken into account by having two capacitive pressure sensors 45.

Figure 16:
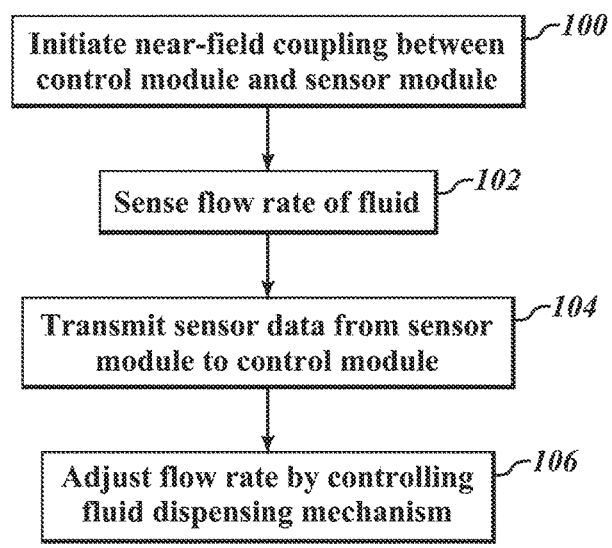
FIG. 16 is a flow diagram of a fluid sensing method according to one embodiment.

FIG. 16 is a flow diagram of a method for controlling the flow rate of a fluid according to one embodiment. At 100, near field coupling is initiated between a sensor module 34 and a control module 32. In particular the control module 32 transmits electromagnetic radiation, for example RF radiation. The sensor module 34 receives the RF radiation and harvests energy therefrom. At 102 the sensor 45 of the sensor module 34 senses the flow rate of the fluid in which the sensor module 34 is placed. At 104 the sensor module 34 transmits flow rate data to the control module 32. The control module 32 receives the flow rate data and compares the flow rate data to an expected flow rate value. At 106 the control module 32 adjusts the flow rate of the fluid by controlling a fluid dispensing mechanism 36. In this manner the flow rate of the fluid can be controlled in a precise manner.

Figure 17:
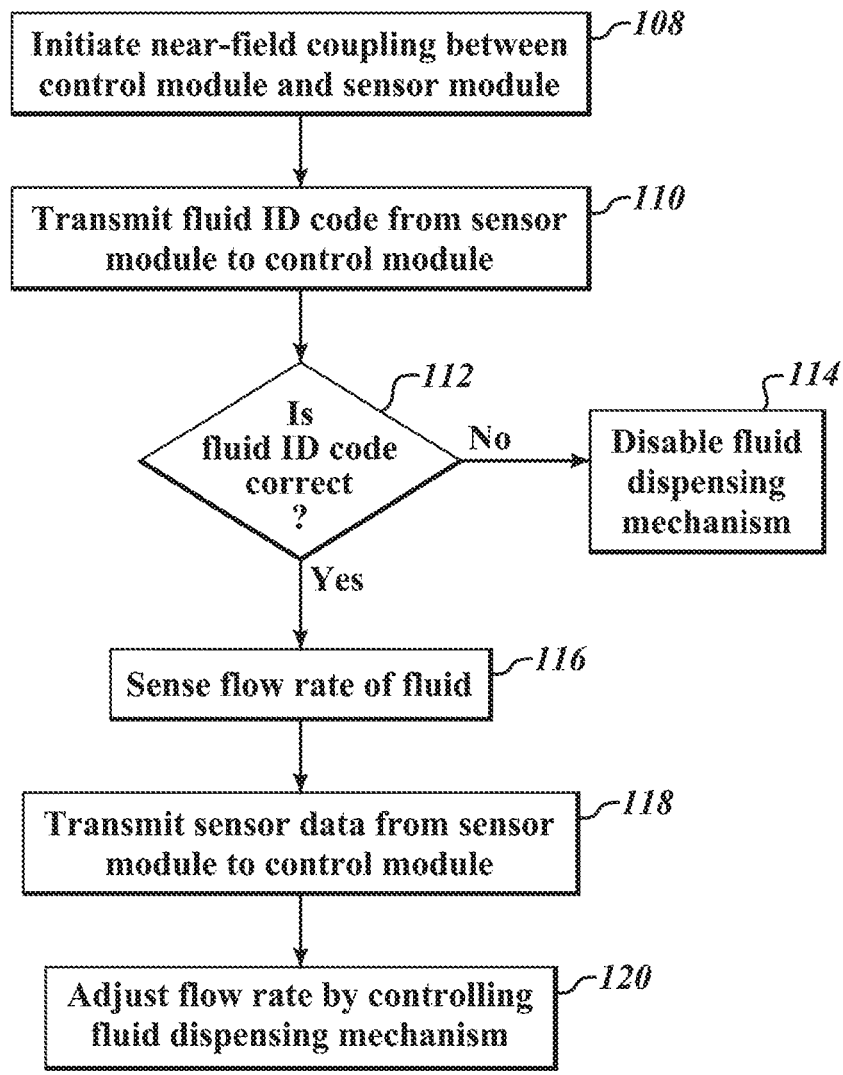
FIG. 17 is a flow diagram of a fluid sensing method according to an alternative embodiment.

FIG. 17 is a flow diagram of a method for controlling the flow rate of a fluid according to an alternative embodiment. At 108, near field coupling is initiated between a sensor module 34 and a control module 32. In particular the control module 32 transmits electromagnetic radiation, for example RF radiation. The sensor module 34 receives the RF radiation and harvests energy therefrom. The control module 32 transmits a request for fluid ID. At 110 the sensor module 34 transmits the fluid ID code of the fluid in which the sensor module 34 is placed.

At 112 the control module 32 checks the fluid ID code to ensure the correct fluid has been provided, prior to the fluid flowing. This can be done by the control module 32 transmitting an interrogation signal to the sensor module 34. In upon receiving the interrogation signal, the sensor module 34 retrieves the fluid ID code from memory 46 and transmits the fluid ID code to the control module 32. If the fluid ID code does not correspond to the expected fluid ID code, the control module 32 disables the fluid dispensing mechanism 36 and prevents fluid from flowing. This can be extremely useful in preventing the wrong drug from being administered to a patient. If the fluid ID code is correct then the control module initiates the fluid dispensing mechanism 36 to begin dispensing the fluid. At 116 the sensor module senses the flow rate of the fluid. At 118 the sensor module 34 transmits flow rate data to the control module 32. The control module 32 receives the flow rate data and compares the flow rate data to an expected flow rate value. At 120 the control module 32 adjusts the flow rate of the fluid by controlling a fluid dispensing mechanism 36. In this manner the flow rate of the fluid can be controlled in a precise manner.

While specific embodiments have been described in relation to the figures, other embodiments and configurations are possible. For example, in one embodiment a cost-effective highly accurate biocompatible sensor module 34 with an integrated temperature sensor at the point of administration, subcutaneously, capable of harvesting ambient energy of some type, for example of heat, kinetic energy, solar energy, RF energy, or any other suitable energy to power itself and communicate via an RF protocol, for example ZigBee® protocol, BTLE protocol, or RFID protocol, with the main system microcontroller of a fluid dispensing system 30 provides accurate flow rates and dose sizes when used in a medical application. For an infusion pump, this could be at the end of the infusion set, while in an auto-injector or syringe pump it could be in the fluid container 40 volumetric chamber, where a unique identifier communicated over the RF protocol to the microcontroller 47 would confirm that the correct drug was being administered, and enable or disable the operation of the pump or injector accordingly.

An added benefit of this mechanism would be to eliminate the possibility of competitors cloning the cassette, or patients unintentionally using counterfeit drugs. The data could also be encrypted, as is currently implemented in near field communication readers and tags, to ensure communication integrity. The data received could be logged for later download as well as used for alarms, such as a free-flow alarm, an improper flow of fluid alarm, an occlusion alarm, an air-in-line alarm, or a dose limit or a Bolus limit exceeded alarm, an empty reservoir alarm, a no reservoir alarm, and a drug mismatch alarm to reduce or eliminate harmful errors. In one embodiment, a sensor module 34 would survive all forms of sterilization, whether it was steam, gamma radiation, or other type of sterilization.

Upon the initial use of the hose or drug container to be used with the infusion pump, the RF interface would provide power to the sensor system 34, authenticate that the drug is compatible with the pump by reading a pre-stored unique ID stored in the memory 46 of the sensor module 34, and then proceed to synchronize the sensor with the RTC from the pump by writing the initial timestamp to the memory 46, which would in turn power up the low power microcontroller 44, start the internal RTC, and then put the system to sleep. After the initial synchronization process, any time an injection is performed, the pump would wake up the sensor over the RF interface via an interrupt on the dual-interface EEPROM 46. The microcontroller 44 would interrogate the sensor 45 and provide real-time feedback over RFID to the main microcontroller 47, allowing for more accurate dosing.

Using a thinned integrated circuit die or dies on flexible plastic for the sensor module 34 allows strain measurement and pressure derivative for various containers 40 and materials. This can be powered solely by the electric field from a control module 32, for example a DEMO-CR95HF-A board. Use of an integrated circuit die allows for a small solution size. The control module 32 and the sensor module 34 can use multiprotocol contactless transceiver IC operating in HF at 13.56 MHz, which can use a wide range of embedded RF applications. There are many suitable RF reader/writer designs for portable and stationary systems. Such a system 30 can be used in a broad range of applications, including computer applications, peripheral applications, consumer applications, industrial applications, healthcare applications, and metering applications. This can be used in compliance with standards such as ISO 15693, ISO 14443A/B and NFC ISO 18092. In one embodiment, the sensor module 34 is placed within an inch of the control module 32. The closer the sensor module 34 is to the control module 32, the more power the sensor module 34 can harvest from the radiation from the control module 32. Any suitable distance can be used which allows the sensor module 34 to harvest energy sufficient to power itself from the radiation transmitted by the control module 32.

In one embodiment, the ASIC 54 has an analog-to-digital converter in addition to energy harvesting circuitry. While a low power microcontroller 44 can be implemented in the ASIC, in one embodiment the ASIC does not have a microcontroller 44 but simply an analog-to-digital converter, suitable memory storage, and energy harvesting circuitry in addition to other circuitry allowing communication between the control module 32, the antenna 43, and the sensor 45. The sensor 45 can be any suitable sensor, including a sensor printed on a substrate, a MEMS sensor, or any other suitable sensor.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method comprising:
   dispensing fluid from a fluid container into a patient;
   sensing, in a sensor module coupled to the fluid container, a fluid parameter of the fluid;
   placing a control module in close proximity to the sensor module, but physically spaced from it by a layer of material;
   powering the sensor module by near field coupling from a control module that is adjacent to the sensor module by passing RF radiation through the layer of material;
   transmitting the fluid parameter as data indicative of the fluid parameter from the sensor module to the control module;
   controlling a flow rate of the fluid by use of the control module based at least in part on the fluid parameter data that was received from the sensor module;
   transmitting data to the sensor module from the control module using near field coupling that passes the data through the layer of material; and
   performing a repeatable feedback series loop of operations, the repeatable feedback series loop of operations including:

transmitting RF radiation from the control module to the sensor module through the layer of material;
after transmitting RF radiation from the control module to the sensor module, transmitting present fluid parameter data from the sensor module as an RF signal back to the control module;
after transmitting the fluid parameter data from the sensor module as an RF signal back to the control module, transmitting a flow rate command based at least in part on the present fluid parameter data from the control module to a fluid dispenser;
after transmitting the flow rate command based at least in part on the present fluid parameter data from the control module to the fluid dispenser, providing an adjusted fluid flow rate of fluid from the fluid dispenser in response to the flow rate command; and
repeating the repeatable feedback series loop of operations at least two more times.

2. The method of claim 1 further comprising transmitting a fluid identification code from the sensor module to the control module.

3. The method of claim 2 wherein the fluid identification code is stored in a memory of the sensor module.

4. The method of claim 3 comprising:
receiving the fluid identification code in the control module; and
dispensing the fluid only if the fluid identification code corresponds to an expected fluid identification.

5. The method of claim 1 wherein the fluid parameter is a pressure of the fluid.

6. The method of claim 1 wherein the fluid parameter is the flow rate of the fluid.

7. The method of claim 1, further comprising transmitting the data as analog data from the control module to the sensor module.

8. The method of claim 1, further comprising converting the data from analog data to digital data by use of a semiconductor integrated circuit die positioned within the fluid when the sensor module is positioned within the fluid.

9. A method, comprising:
transmitting data from a sensor module that is positioned within a fluid through a layer of material using a near field communication protocol;
powering the sensor module that is positioned within the fluid by sending a power signal from a control module to the sensor module through the layer of material;
sensing a fluid parameter of a fluid that is adjacent to the sensor module and in physical contact therewith;
sensing a temperature parameter of the fluid in addition to the fluid parameter of the fluid;
transmitting, via a near field coupling protocol, data indicating the sensed fluid parameter and temperature parameter from the sensor module to the control module by passing the data through the layer of material;
outputting a signal from the control module to a dispensing mechanism that causes the fluid to be dispensed at a controllable rate;
dispensing the fluid from a fluid container at a controlled rate; and
providing feedback to adjust the controlled rate of the dispensed fluid, the feedback including repeating, in the following order, the operations of:
sending the power signal from the control module to the sensor module through the layer of material;
transmitting through the near field coupling protocol data indicating the present sensed fluid parameter and temperature parameter from the sensor module to the control module;
providing in the control module a flow rate command based at least in part on the present sensed fluid parameter and temperature parameter;
transmitting the flow rate command from the control module to the dispensing mechanism; and
dispensing the fluid from the fluid container at a current controlled rate that is based on the flow rate command.

10. The method according to claim 9, further comprising dispensing the fluid into a patient.

11. The method according to claim 9, wherein the fluid is insulin.

12. The method according to claim 9, wherein the fluid parameter is a pressure of the fluid.

13. The method according to claim 12, further comprising:
outputting the temperature data from the sensor module to the control module; and
varying the fluid flow rate based at least in part on the temperature of the fluid being dispensed.

14. A method comprising:
dispensing fluid from a fluid container into a patient;
sensing, in a sensor module coupled to the fluid container, a pressure parameter of the fluid, the pressure parameter indicating a pressure of the fluid;
placing a control module in close proximity to the sensor module, but physically spaced from it by a layer of material;
powering the sensor module by near field coupling from a control module that is adjacent to the sensor module by passing RF radiation through the layer of material;
transmitting the pressure parameter as data indicative of the pressure parameter from the sensor module to the control module;
controlling a flow rate of the fluid by use of the control module based at least in part on the pressure parameter data that was received from the sensor module;
transmitting data to the sensor module from the control module using near field coupling that passes the data through the layer of material; and
performing a repeatable feedback series loop of operations, the repeatable feedback series loop of operations including:
transmitting RF radiation from the control module to the sensor module through the layer of material;
after transmitting RF radiation from the control module to the sensor module, transmitting present pressure parameter data from the sensor module as an RF signal back to the control module;
after transmitting the pressure parameter data from the sensor module as an RF signal back to the control module, transmitting a flow rate command based at least in part on the present pressure parameter data from the control module to a fluid dispenser;
after transmitting the flow rate command based at least in part on the present pressure parameter data from the control module to the fluid dispenser, providing an adjusted fluid flow rate of fluid from the fluid dispenser in response to the flow rate command; and
repeating the repeatable feedback series loop of operations at least two more times.

15. The method of claim 14, further comprising transmitting a fluid identification code from the sensor module to the control module.

16. The method of claim 15 wherein the fluid identification code is stored in a memory of the sensor module.

17. The method of claim 16, further comprising:
receiving the fluid identification code in the control module; and
dispensing the fluid only if the fluid identification code corresponds to an expected fluid identification.

18. The method of claim 14, further comprising transmitting the data as analog data from the control module to the sensor module.

19. The method of claim 15, further comprising converting the data from analog data to digital data by use of a semiconductor integrated circuit die positioned within the fluid when the sensor module is positioned within the fluid.

\* \* \* \* \*